United States Patent
Mizuta et al.

(10) Patent No.: US 9,618,434 B2
(45) Date of Patent: Apr. 11, 2017

(54) STIFFNESS MEASUREMENT METHOD AND DEVICE

(71) Applicant: ADVICS CO., LTD., Kariya (JP)

(72) Inventors: Kazuho Mizuta, Kariya (JP); Yukio Nishizawa, Toyoake (JP); Kyoko Kosaka, Anjyo (JP); Yutaka Kurita, Higashiosaka (JP); Yasunori Oura, Kyoto (JP)

(73) Assignee: ADVICS CO., LTD., Kariya, Aichi-Pref (JP)

( * ) Notice: Subject to any disclaimer, the term of this patent is extended or adjusted under 35 U.S.C. 154(b) by 227 days.

(21) Appl. No.: 14/397,767

(22) PCT Filed: May 31, 2013

(86) PCT No.: PCT/JP2013/065195
§ 371 (c)(1),
(2) Date: Oct. 29, 2014

(87) PCT Pub. No.: WO2013/180268
PCT Pub. Date: Dec. 5, 2013

(65) Prior Publication Data
US 2015/0128716 A1    May 14, 2015

(30) Foreign Application Priority Data
May 31, 2012    (JP) ................. 2012-125002

(51) Int. Cl.
*G01N 3/08* (2006.01)
*G01N 3/32* (2006.01)
*G01L 5/28* (2006.01)

(52) U.S. Cl.
CPC ............... *G01N 3/08* (2013.01); *G01N 3/32* (2013.01); *G01L 5/28* (2013.01)

(58) Field of Classification Search
CPC .... G01L 5/28; G01N 2203/0075; G01N 3/08; G01N 3/20; G01N 3/32
(Continued)

(56) References Cited

U.S. PATENT DOCUMENTS 5,689,058 A * 11/1997 Yuan ............... G01N 19/02
  73/9
6,145,382 A * 11/2000 Nagasawa ......... G01N 19/02
  73/432.1
(Continued)

FOREIGN PATENT DOCUMENTS

| JP | 9-152392 A | 6/1997 |
|---|---|---|
| JP | 4059836 B2 | 12/2007 |
| JP | 2010-185792 A | 8/2010 |

OTHER PUBLICATIONS

International Search Report (PCT/ISA/210) mailed on Aug. 6, 2013, by the Japanese Patent Office as the International Searching Authority for International Application No. PCT/JP2013/065195.
(Continued)

*Primary Examiner* — Freddie Kirkland, III
(74) *Attorney, Agent, or Firm* — Buchanan Ingersoll & Rooney PC

(57) ABSTRACT

A calculating device of the stiffness measurement device pressurizes an object to be measured with a predetermined pressure and the stiffness of the object to be measured in the squeal frequency band is calculated based on an inclination of a stress-displacement performance curve immediately after a start of depressurization after the pressurization. According to this device, there is no need to oscillate the object with a high frequency band and there is no need to enhance the stiffness of the housing of the measurement device, which leads to a downsizing of the device. Further, there is no need for measuring of acceleration speed of the
(Continued)

object to be measured and accelerator can be eliminated to reduce the cost of the stiffness measurement device.

3 Claims, 6 Drawing Sheets

(58) Field of Classification Search
USPC .................................................. 73/121, 790
See application file for complete search history.

(56) References Cited

U.S. PATENT DOCUMENTS

| | | | | |
|---|---|---|---|---|
| 6,382,027 B1* | 5/2002 | Uhlig | ...................... | G01N 29/14 73/579 |
| 7,380,443 B2* | 6/2008 | Tsujii | ....................... | G01N 3/42 73/81 |
| 7,441,465 B2* | 10/2008 | Oliver | ....................... | G01N 3/32 73/760 |
| 8,204,699 B2* | 6/2012 | Sakai | ....................... | G01N 3/20 702/150 |
| 8,528,392 B2* | 9/2013 | Thomas | .................... | G01L 5/28 73/121 |
| 8,766,811 B2* | 7/2014 | Spampinato | ............. | G01N 3/08 340/665 |
| 8,839,671 B2* | 9/2014 | Sueki | ....................... | G01B 5/06 73/573 |
| 9,116,080 B2* | 8/2015 | Spampinato | ............. | G01N 3/08 73/573 |
| 2007/0295091 A1* | 12/2007 | Oliver | ...................... | G01N 3/32 73/573 |
| 2010/0204932 A1* | 8/2010 | Sakai | ....................... | G01N 3/20 702/42 |

OTHER PUBLICATIONS

Yasunori Oura et al., Influence of Dynamic Stiffness in a Contact Region on Disk Brake Squeal, Dynamic and Design Conference, Sep. 27, 2004, vol. 2004, pp. 1-9.

* cited by examiner

STIFFNESS MEASUREMENT METHOD AND DEVICE

TECHNICAL FIELD

This invention relates to a method and a device for measuring the stiffness of an object to be measured and more particularly to a method and a device for measuring the stiffness (equivalent value) of a friction pad material in a squeal frequency band for a brake disc device.

BACKGROUND ART

A disc brake device adapted to a vehicle brake device sometimes generates a so-called squeal noise when the brake is applied. This squeal noise is considered to be generated due to a coupled oscillation of the disc plate and the friction pad material and a study has been made focusing on the frictional contact portion between the disc plate and the friction pad material, between which the force transmitting is made (See non-patent literature 1). At the early stage of the study, a model analysis of a contact point where vibration occurs with the same phase and the same amplitude in the friction contact portion was conducted. According to the analysis, a qualitative tendency of the squeal could be represented, but a restoration moment about the contact point could not be taken into consideration and as a result, the qualitative tendency of the squeal did not agree with the quantitative tendency. Accordingly, in order to solve this problem, it is necessary to conduct the model analysis of the contact surface by measuring the stiffness of the dynamic stiffness of the contact surface.

In the non-patent literature 1, as a measurement device for measuring the dynamic stiffness of the contact surface, a device equipped with an oscillation device for oscillating the friction pad material under a pressurized state, a load measurement device which measures the load applied to the friction pad material and an acceleration measurement device which measures the acceleration of the friction pad material generated by the oscillation. This dynamic stiffness measurement device first oscillates the friction pad material with a random wave of squeal oscillation frequency band (1 kHz to 5 kHz) and measures the acceleration speed of the friction pad material generated by the oscillation. Thus, the transfer function (Accelerance) from the force to the acceleration is obtained and the resulted value is converted into the dynamic stiffness. Further, a device similar to the device above is disclosed in the patent literature 1, although the device disclosed therein relates to a measurement device for measuring the spring constant.

CITATION LIST

Patent Literature

Patent Literature 1: JP4059836B2

Non-Patent Literature

Non-patent literature 1: "Influence of Dynamic Stiffness in a Contact Region on Disk Brake Squeal", No. 614 of CD-ROM Thesis Paper, Dynamics and Design Conference 2004 Vol. No. 04-5, The Japan Society of Mechanical Engineers.

SUMMARY OF INVENTION

Technical Problem(s)

According to the dynamic stiffness measurement device of the above mentioned literatures, it is necessary to first obtain a transfer function (Accelerance) from the force to the acceleration and then to convert the obtained result into the stiffness. Accordingly, this device has a tendency of becoming complicated. Further, according to this device, it is necessary to oscillate the friction pad material with a relatively high frequency and accordingly, it is necessary to enhance the stiffness of housing of the dynamic stiffness measurement device. This may lead to an increase of size of the device. Further, it is necessary to measure the acceleration speed of the friction pad material and an acceleration measurement device has to be equipped, which leads to an increase of cost in manufacturing the dynamic stiffness measurement device.

Accordingly, this invention was made in consideration with the above-mentioned situation and the objective of the invention is to provide a stiffness measurement method which can easily measure the stiffness (equivalent value) of an object to be measured in the squeal frequency band and to provide a stiffness measurement device which is small in size and low in cost.

Solution to Problem(s)

The method for measuring a stiffness of an object to be measured in a squeal frequency band according to the invention associated with a first aspect includes a supporting step for supporting the object to be measured, a pressurizing step for pressurizing the object to be measured which has been supported, a gradual depressurizing step for gradually depressurizing the object to be measured after a pressure applied thereto by the pressurizing step has reached to a predetermined value, a measuring step for measuring the pressure applied to and the pressure depressurized from the object to be measured and a displacement of the object to be measured when the object to be measured is pressurized and depressurized at the steps of the pressurizing step and the gradual depressurizing step and a calculating step for calculating the stiffness of the object to be measured in the squeal frequency band based on an inclination of a stress-displacement performance curve immediately after a start of the depressurizing step for gradually depressurizing the pressure applied to the object to be measured.

The invention associated with a second aspect pertains to a stiffness measurement device which measures the stiffness of an object to be measured in a squeal frequency band. The stiffness measurement device includes a support device which supports the object to be measured, a pressurizing device which can pressurize and/or depressurize the object to be measured which has been supported by the support device, a pressure measurement device which measures a pressure to be applied to or depressurized from the object to be measured, a displacement measurement device which measures a displacement of the object to be measured when the object to be measured is pressurized or depressurized and a calculating device which calculates the stiffness of the object to be measured in the squeal frequency band based on an inclination immediately after a start of a depressurization in a stress-displacement performance diagram by obtaining the stress-displacement diagram upon the depressurization after the pressurization of the object to be measured to a predetermined pressure level.

The invention associated with a third aspect is characterized in that stiffness measurement device as set forth in the second aspect includes the pressurizing device which gradually depressurizes the pressure of the object to be measured and the displacement measurement device which measures the displacement of the object to be measured at the time of a gradual depressurizing.

The invention associated with a fourth aspect is characterized in that the object to be measured as set forth in the second aspect or the third aspect includes a friction pad material of a disc brake and the calculating device which calculates the stiffness of the object to be measured in the squeal frequency band based on the inclination that the displacement of the object to be measured has reached to an amplitude of oscillation of squeal of the friction pad material.

According to the invention associated with the first aspect, the stiffness of the object to be measured in the squeal frequency band is calculated based on an inclination of a stress-displacement performance curve (diagram) immediately after a start of depressurization in the step for gradually depressurizing a pressure applied to the object to be measured, after a pressurization of the object to be measured to a predetermined pressure level. Accordingly, the stiffness of the object to be measured in the squeal frequency band can be easily measured without obtaining a transfer function (Accelerance) transferring from a force to acceleration and converting the obtained result of the transfer function into the dynamic stiffness, which conventionally was necessary.

According to the invention associated with the second aspect, the calculating device calculates the stiffness of the object to be measured in the squeal frequency band based on the inclination immediately after the start of depressurization in a stress-displacement diagram upon a gradual depressurization after pressurization of the object to be measured to a predetermined pressure level. Accordingly, since there is no need to oscillate the object to be measured with a high frequency and further no need to enhance stiffness of the housing as required in the conventional device, the device as a whole can be down-sized. Further, according to the invention, there is no need to measure the acceleration of the object to be measured as was necessary for the conventional device, the acceleration measurement device can be omitted which leads to a cost reduction.

According to the invention associated with the third aspect, the displacement of the object to be measured when the object is gradually depressurized. Accordingly, a displacement measurement device which can measure a displacement of an object relatively in a low frequency band can be used.

According to the invention associated with the fourth aspect, the stiffness of a contact surface between the disc plate and the friction pad material in a squeal frequency band can be obtained. Accordingly, by analyzing the contact surface model, the squeal generated by coupled oscillation between the disc plate and the friction pad material can be quantitatively represented.

DESCRIPTION OF EMBODIMENTS

Figure 1:
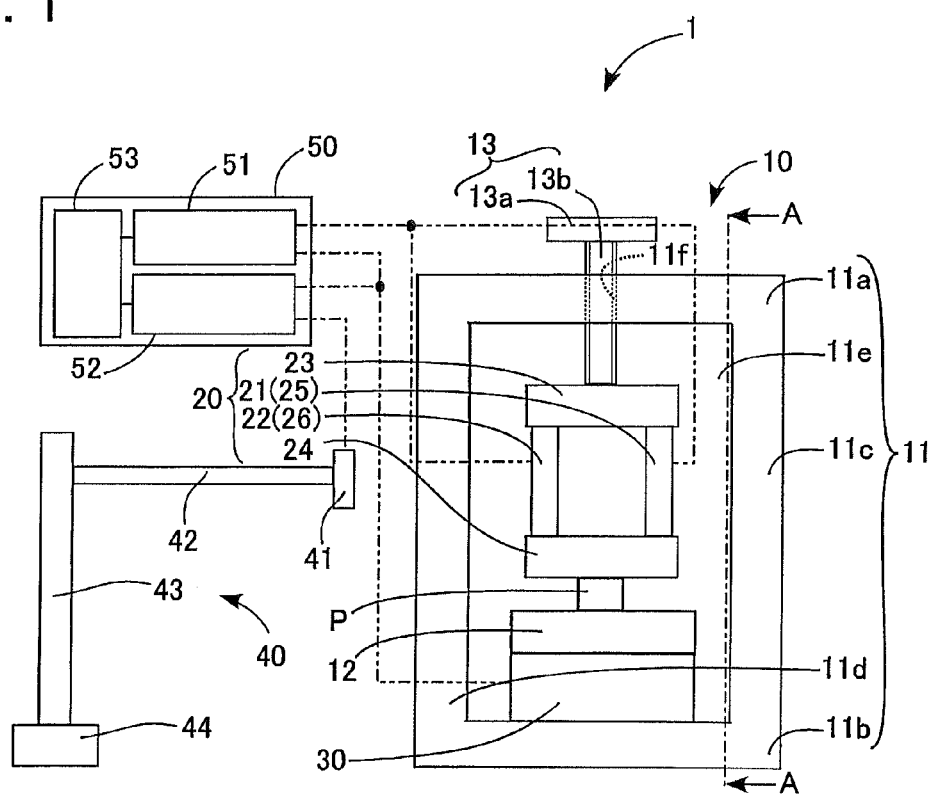
FIG. 1 is a general view of a stiffness measurement device according to an embodiment of the invention.

The embodiment of the present invention will be explained below with reference to the attached drawings. As shown in FIG. 1, the stiffness measurement device 1 according to the embodiment includes a support device 10 which supports an object to be measured P (for example, a test piece cut from a friction pad material of a disc brake device), a pressurizing device 20 which pressurizes the object to be measured P supported by the support device 10 or depressurizes the pressure of the object to be measured P which has been pressurized, a pressure measurement device 30 which measures the pressure to be applied to or depressurized from the object to be measured P, a displacement measurement device 40 which measures a displacement of the object to be measured P when the object to be measured P is pressurized or depressurized and a control device 50 which inputs the measurement data sent from the pressure measurement device 30 and the displacement measurement device 40.

The support device 10 includes a housing 11, a mount 12 for mounting the object to be measured P and a fixing screw 13 which fixes the object to be measured P to the mount 12. The housing 11 is formed to be a box-shape having upper portion 11a, a bottom portion 11b side portions 11c and 11d and a back portion 11e. The mount 12 is fixed to the bottom portion 11b of the housing 11 together with the pressure measurement device 30, the structure of which will be explained later. The fixing screw 13 includes a handle portion 13a and a male screw portion 13b provided on the handle portion 13a and projecting downwardly therefrom to penetrate through the upper portion 11a of the housing 11 located lower side relative to the handle portion 13a of the fixing screw 13. The male screw portion 13b is mated with a female screw portion 11f which is provided in the upper portion 11a and penetrating therethrough.

The pressurizing device 20 includes four columnar actuators 21, 22, 25 and 26 and two fixing plates 23 and 24 for fixing the actuators 21, 22, 25 and 26 by sandwiching by the two fixing plates. The actuators 25 and 26 are located behind the actuators 21 and 22 (See FIG. 3), respectively. These actuators 21, 22, 25 and 26 are the actuators such as layered piezoelectric actuators which are extendible or compressible by an electric power of sine waves or triangle waves. The four actuators 21, 22, 25 and 26 are arranged at four corners of the fixing plates 23 and 24 in parallel with each other, respectively. The upper surfaces and the under surfaces of the four actuators 21, 22, 25 and 26 are fixed to the fixing plates 23 and 24, respectively.

The pressurizing device 30 is for example, a crystal piezoelectric type force sensor and is fixed to the upper surface of the bottom portion 11b of the housing 11. The pressurizing device 30 includes a sensor portion (not shown) on an upper portion. The mount 12 is mounted on this sensor portion.

The displacement measurement device 40 includes a sensor portion 41, a support arm 42 which supports the sensor portion 41 at one end portion, a support shaft 43 movably supporting the other end portion of the support arm 42 in an up-down direction and a stand 44 from which the support shaft 43 is erected. The sensor portion 41 is an eddy current type displacement sensor which can measure the displacement amount of the object to be measured P which is depressurized or pressurized by the extendible or compressible actuators 21, 22, 25 and 26 by the electric power of relatively low frequency sine waves or triangle waves. The support arm 42 is slidable along the support shaft 43 and is fixed thereto by a screw (not shown) at any desired height position.

The control device 50 inputs the measurement data from the pressure measurement device 30 and includes a pressure control device 51 which controls the pressurization and depressurization operation of the pressurizing device 20, a calculating device 52 which calculates the stiffness of the object to be measured in the squeal frequency band by inputting the measurement data from the pressure measurement device 30 and the displacement measurement device 40 and a memory device 53 which memorizes pressure control program for controlling the above pressure.

Figure 2:
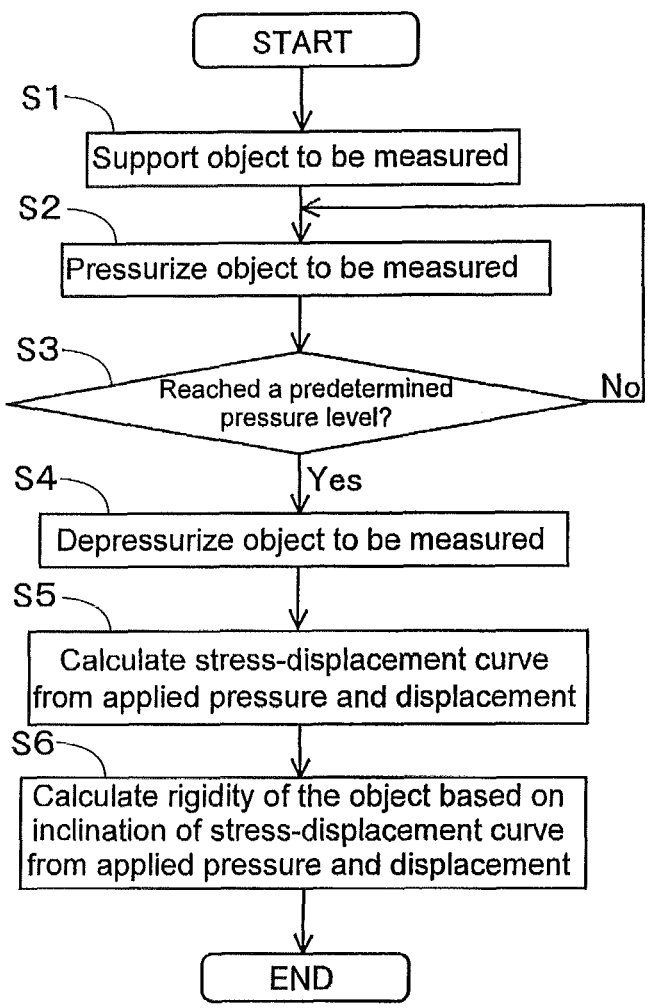
FIG. 2 is a flowchart explaining an operation of the stiffness measurement device according to the embodiment.
Figure 3:
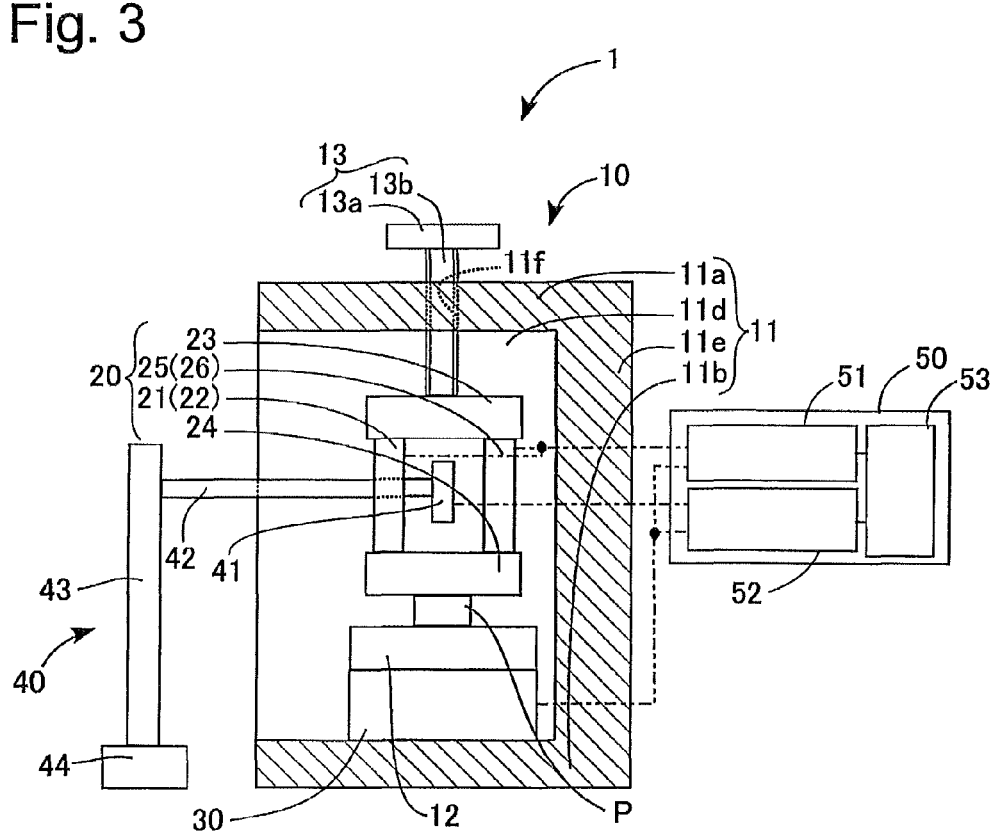
FIG. 3 is a cross sectional view of the stiffness measurement device according to the embodiment taken along the line A-A in FIG. 1, showing a state that the measurement preparation has been completed.

Next, operation of the measurement by the stiffness measurement device 1 will be explained hereinafter with reference to the flowchart illustrated in FIG. 2. First, as a preparation process work, the friction pad material is cut out to make a test piece to be an object to be measured P. The cut test piece is mounted on the mount 12 positioned lower side of the fixing plate 24 of the pressurizing device 20. Then the handle portion 13a of the fixing screw 13 is rotated to have the lower end portion of the male screw portion 13b to be brought into contact with the upper surface of the fixing plate 23 so that the object to be measured P (test piece) is fixed between the fixing plate 24 and the mount 12 by sandwiching therebetween. Then the sensor portion 41 of the displacement measurement device 40 is inserted between the actuators 21, 22, 25 and 26 of the pressurizing device 20. Then the support arm 42 is slidably moved along the support shaft 43 to fix a position (height position) where the lower end portion of the sensor portion 41 is separated with a predetermined distance (which is a distance enable to sense) from the upper surface of the fixing plate 24 of the pressurizing device 20. The change of the distance between the sensor portion 41 and the fixing plate 24 is measured as the displacement of the object to be measured P. Thus, as shown in FIG. 3, the supporting process for the object to be measured P is completed (step S1).

The pressure control device 51 of the control device 50 pressurizes the friction pad material (object to be measured P) by controlling the pressurizing device 20 (at the step S2). In more detail, the pressure control device 51 reads out the pressure control program from the memory device 53 and then supplies the actuators 21, 22, 25 and 26 with the sine wave electric power of a frequency with 0.1 Hz in a direction that the amplitude thereof becomes large so that the actuators are extended to pressurize the object to be measured P by the fixing plate 24.

The pressure control device 51 judges whether the pressure received by the object to be measured P reached to a predetermined pressure value or not (at the step S3) and if the pressure is judged to have reached to the predetermined pressure level, the object to be measured P is depressurized by controlling the pressurizing device 20 (at the step s4). In more detail, when the pressure of the object to be measured P reaches to the value of 1 MPa which corresponds to the pressure upon braking operation, the pressure control device 51 supplies the actuators 21, 22, 25 and 26 with the sine wave electric power 0.1 Hz in a direction where the amplitude of frequency is reduced. Thus, the actuators 21, 22, 25 and 26 are compressed to gradually depressurize the pressing force to the object to be measured P to finally depressurize the applied pressure thereto on the fixing plate 24.

Figure 4:
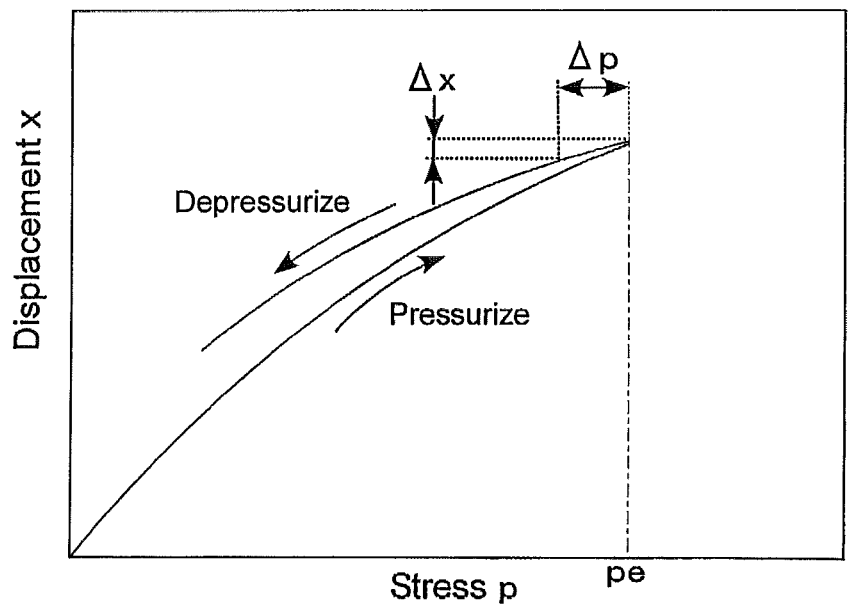
FIG. 4 is a stress-displacement diagram measured by the stiffness measurement device according to the embodiment.

The calculating device 52 obtains a relationship between the stress and displacement of the object to be measured P by inputting the pressure and the displacement of the object to be measured P when pressurized or depressurized from the pressure measurement device 30 and the displacement measurement device 40 (at the step S5). Then the stiffness of the object to be measured P in the squeal frequency band based on the inclination immediately after the start of depressurization in a stress-displacement diagram is obtained and the obtained stiffness is memorized in the memory device 53 (at the step S6). In more detail, the calculating device 52 calculates and obtains the stress "p" and displacement "x" relationship diagram upon pressurizing and depressurizing the object to be measured P as shown in FIG. 4. It is noted that by gradually depressurizing, the change of the curve of the stress "p" and displacement "x" relationship diagram upon depressurization becomes gentler than the change upon pressurization of the object to be measured P as shown in FIG. 4. First, the inclination $\Delta x/\Delta p$ is obtained based on the stress change amount $\Delta p$ when the displacement change amount $\Delta x$ of the object to be measured P immediately after the start of depressurization from a predetermined pressure "pe" in the curve of the stress "p" and displacement "x" relationship diagram reached to a predetermined amplitude of squeal oscillation of the friction pad material, for example the amplitudes of 0.1 μm, 1.0 μm and 10 μm. Thus obtained inclination value is inversed to be defined as the stiffness in the squeal frequency band and memorized in the memory device 53. Thus, the measurement operation of the stiffness measurement device 1 is completed.

Figure 5:
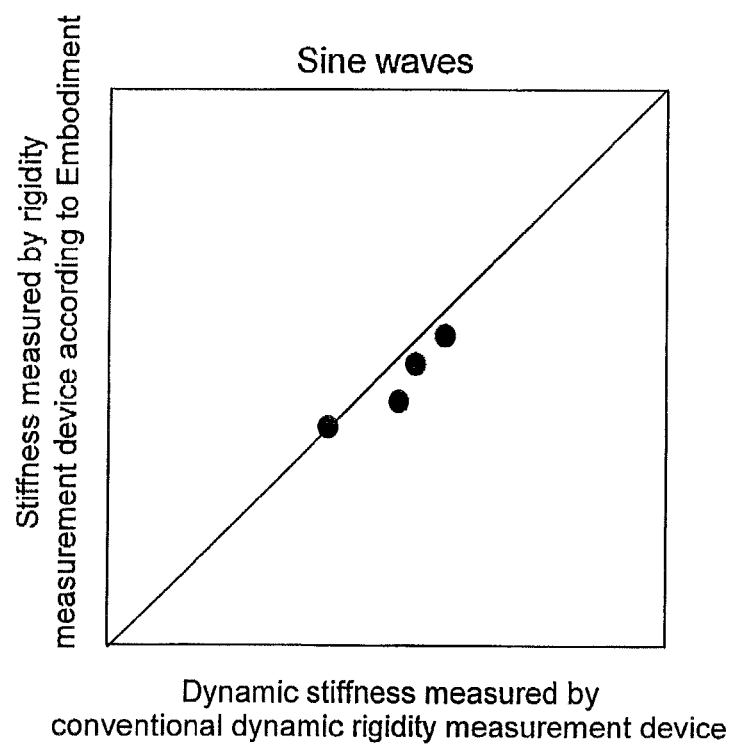
FIG. 5 is a graph showing a relationship between the stiffness in the squeal frequency band measured by using a sine wave by the pressurizing device of the stiffness measurement device according to the embodiment of the invention and the dynamic stiffness measured by a conventional dynamic stiffness measurement device.

The comparison result of dynamic stiffness of four objects to be measured P are shown in FIG. 5. The comparison was made between the measurement of the stiffness measured by the stiffness measurement device according to the embodiment of the invention and the dynamic stiffness measured by a conventional dynamic stiffness measurement device. As clearly shown in FIG. 5, the stiffness of the object to be measured P in the squeal frequency band obtained by the stiffness measurement device 1 according to the embodiment and the dynamic stiffness of the object to be measured P obtained by the conventional dynamic stiffness measurement device are mutually related one for one with each other. Therefore, an analysis on a model of contact surface between the disc plate and the friction pad material can be made by using the stiffness of the object to be measured P in the squeal frequency band which is obtained by the stiffness measurement device 1 according to the embodiment of the invention.

Figure 6:
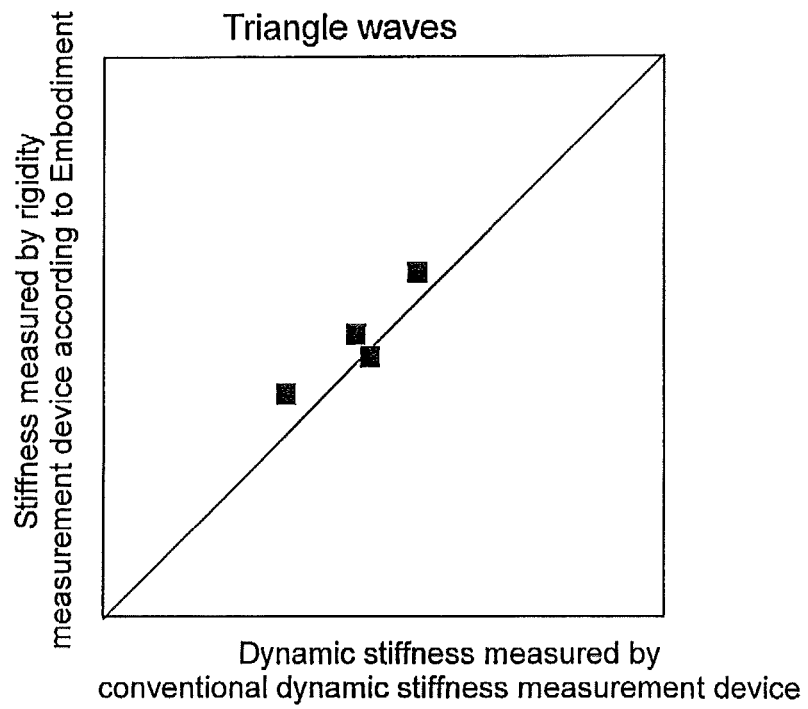
FIG. 6 is a graph showing a relationship between the stiffness in the squeal frequency band measured by using a triangle wave by the pressurizing device of the stiffness measurement device according to the embodiment of the invention and the dynamic stiffness measured by a conventional dynamic stiffness measurement.

Further, instead of using frequency of 0.1 Hz sine wave electric power, a frequency of 0.1 Hz triangle wave electric power is supplied to the actuators 21, 22, 25 and 26 to obtain the stiffness of four objects to be measured P in the squeal frequency band and the dynamic stiffness of four objects to be measured P obtained by the conventional dynamic stiffness measurement device. The comparison result of the stiffness obtained by the embodiment of the invention and the dynamic stiffness obtained by the conventional dynamic stiffness measurement device is shown in FIG. 6. As clear from FIG. 6, the stiffness of the object to be measured P in the squeal frequency band obtained by using the frequency of 0.1 Hz triangle wave electric power and the dynamic stiffness of the object to be measured obtained by the conventional dynamic stiffness measurement device are mutually related one for one and accordingly, an analysis on a model of contact surface between the disc plate and the friction pad material can be made by using the stiffness of the object to be measured P in the squeal frequency band which is obtained by using frequency of 0.1 Hz triangle wave electric power.

Figure 7:
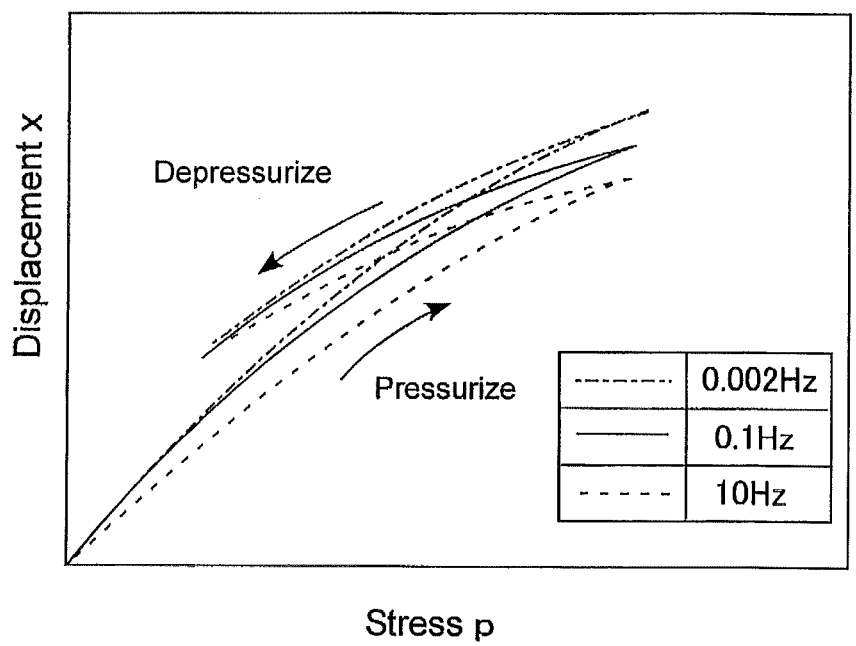
FIG. 7 is a stress-displacement diagram showing the relationship between the stress and the displacement measured by changing the frequency by the pressurizing device of the stiffness measurement device according to the embodiment.
Figure 8:
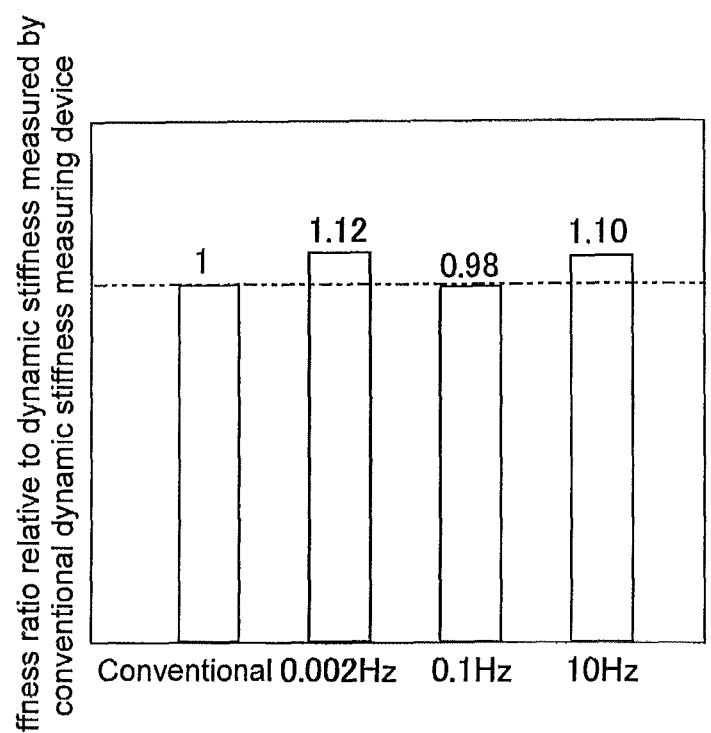
FIG. 8 is a graph showing ratio of the stiffness in the squeal frequency band measured by changing the frequency by the pressurizing device of the stiffness measurement device according to the embodiment relative to the dynamic stiffness measured by the conventional measurement device.

Still further, other than the frequency of 0.1 Hz sine waves, frequencies of 0.002 Hz and 10 Hz sine waves electric power supplied to the actuators 21, 22, 25 and 26 are shown in FIG. 7 as the stress "p" and the displacement "x" relationship diagram. The result of the comparison between the stiffness of the object to be measured P in the squeal frequency band and the dynamic stiffness of the object to be measured P is shown in FIG. 8. It is noted that the stiffness in FIG. 8 was obtained based on the inclination in the stress "p" and displacement "x" relationship diagram when the displacement change amount Δx of the object to be measured P immediately after the start of depressurization from the predetermined pressure level reached to the value of 0.2 μm. As seen from the graph in FIG. 7, tendencies of the stress "p" and displacement "x" relationship diagrams in each case where the 0.002 Hz, 0.1 Hz and 10 Hz frequency sine waves electric powers are supplied to the actuators 21, 22, 25 and 26 are approximately the same and as apparent from FIG. 8, the stiffness of the object to be measured in the squeal frequency band is approximately the same with the dynamic stiffness of the object to be measured P obtained by the conventional dynamic stiffness measurement device and accordingly, an analysis on a model of contact surface between the disc plate and the friction pad material can be made by using the stiffness of the object to be measured P in the squeal frequency band which is obtained by using frequencies of 0.002 Hz and 10 Hz frequency waves electric power.

Figure 9:
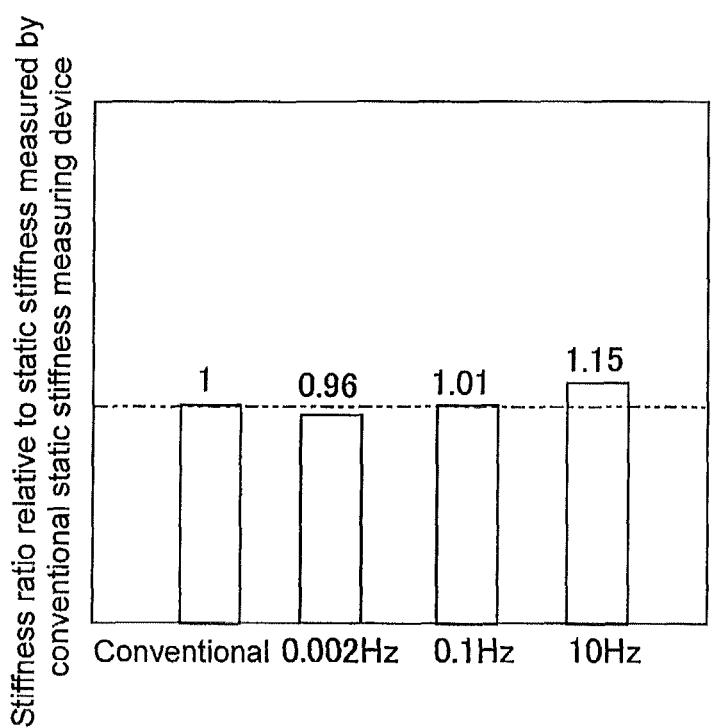
FIG. 9 is a graph showing ratio of the static stiffness measured by changing the frequency by the pressurizing device of the stiffness measurement device according to the embodiment relative to the static stiffness measured by the conventional measurement device.

FIG. 9 shows the result of comparison between the static stiffness p/x obtained from the stress p and the displacement x when the frequency of 0.002 Hz, 0.1 Hz and 10 Hz sine waves electric power in a direction where the frequency oscillation becomes large, is applied to the actuators 21, 22, 25 and 26 (upon pressurization operation) and the static stiffness of the object to be measured P obtained by a conventional static stiffness measurement device (for example, an Instron make 5582 Type material testing machine). As apparent from FIG. 9, each static stiffness of the objects to be measured P is approximately the same with the static stiffness of the object to be measured P measured by the conventional static stiffness measurement device. Thus, the stiffness and the static stiffness of the object to be measured P in the squeal frequency band can be obtained simultaneously according to the stiffness measurement device 1 of the embodiment of the invention.

As explained in the embodiment of the invention, the pressurizing device 20 is operated to pressurize/depressurize the object to be measured P by using sine wave and triangle wave electric powers to be supplied to the actuators 21, 22, 25 and 26 to make simple in structure. If as long as a gradual depressurizing can be available, the pressurizing operation need not be carried out with the same way as the depressurizing operation. For example, the pressurization may be carried out very quickly, instead. According to this embodiment, layered piezoelectric actuators are used for the actuators 21, 22, 25 and 26. However, a hydraulic type actuator can be used, instead. In addition, according to the embodiment, an eddy current type displacement sensor is used for the displacement measurement device 40, however, laser type or electrostatic type displacement actuator may be used, instead.

According to the stiffness measurement device 1 of the embodiment of the invention, the stiffness of the object to be measured P in the squeal frequency band can be measured without any particular exclusive use of dynamic stiffness measurement device, merely using an existing static compression testing machine. The stiffness of the object to be measured P in the squeal frequency band can be easily and simply measured. There is no need to oscillate the object to be measured with a high frequency as was necessary in a conventional method and accordingly, there is no need to enhance the stiffness of the housing of the device, which may lead to the downsizing of the device. Further, according to the conventional device, if the object to be measured P has to be oscillated with a high frequency, the output of the oscillator has to be enhanced to cope with a large object to be measured and accordingly, the size of the object has to be limited to an extent. According to the stiffness measurement device 1 of the embodiment of the invention, since it is not necessary to oscillate with a high frequency, the size of the object to be measured can be extended such as for example, to a full-size friction pad material.

The invention claimed is:

1. A stiffness measurement method for measuring a stiffness of an object to be measured in a squeal frequency band, the method comprising:

supporting step for supporting the object to be measured;

a pressurizing step for pressurizing the object to be measured which has been supported;

a gradual depressurizing step for gradually depressurizing the object to be measured by using an oscillation frequency that is smaller than the squeal frequency band of the object to be measured after a pressure applied thereto by the pressurizing step has reached to a predetermined value;

a measuring step for measuring the pressure applied to and the pressure depressurized from the object to be measured and a displacement of the object to be measured when the object to be measured is pressurized and depressurized at the steps of the pressurizing step and the gradual depressurizing step; and a calculating step for calculating the stiffness of the object to be measured in the squeal frequency band based on an inclination that is obtained based on a stress change amount when the displacement change amount of the object to be measured immediately after the start of depressurization from the predetermined value in a curve of a stress and displacement relationship diagram has reached to an amplitude of squeal oscillation of the object to be measured.

2. A stiffness measurement device which measures a stiffness of an object to be measured in a squeal frequency band, comprising:

a support device which supports the object to be measured;

a pressurizing device which can pressurize the object to be measured which has been supported by the support device and can gradually depressurize the object to be measured by using an oscillation frequency that is smaller than the squeal frequency band of the object to be measured after a pressure applied thereto has reached a predetermined value;

a pressure measurement device which measures a pressure to be applied to or depressurized from the object to be measured;

a displacement measurement device which measures a displacement of the object to be measured when the object to be measured is pressurized or depressurized; and a calculating device which calculates the stiffness of the object to be measured in the squeal frequency band based on an inclination that is obtained based on a stress change amount when the displacement change amount of the object to be measured immediately after the start of depressurization from the predetermined value in a curve of a stress and displacement relationship diagram has reached to an amplitude of squeal oscillation of the object to be measured.

3. The stiffness measurement device according to claim 2, wherein the object to be measured includes a friction pad material of a disc brake.

* * * * *